United States Patent [19]

Cottrell et al.

[11] Patent Number: 5,104,989
[45] Date of Patent: Apr. 14, 1992

[54] CHIRAL SYNTHESIS FOR PRODUCING 1-AZABICYCLO[2.2.1]HEPTANE-3-CARBOXYLATES

[75] Inventors: I. Cottrell, Hertfordshire; S. H. B. Wright, Sawbridgeworth; D. Hands, Oakwood, all of England

[73] Assignee: Merck Sharp & Dohme Ltd., Hertfordshire, England

[21] Appl. No.: 520,945

[22] Filed: May 9, 1990

[30] Foreign Application Priority Data

May 15, 1989 [GB] United Kingdom ............... 8911080

[51] Int. Cl.⁵ .................... C07D 221/02; C07D 453/02
[52] U.S. Cl. ................................... 546/112; 548/452
[58] Field of Search .................... 546/200, 133, 112; 548/452

[56] References Cited

U.S. PATENT DOCUMENTS 4,788,305  11/1988  Tessier et al. ................... 549/463

FOREIGN PATENT DOCUMENTS 239309   9/1987  European Pat. Off. .
257741   3/1988  European Pat. Off. .
261763   3/1988  European Pat. Off. .
398629  11/1990  European Pat. Off. .
8911081  5/1989  United Kingdom .

*Primary Examiner*—C. Warren Ivy
*Assistant Examiner*—Raymond Covington
*Attorney, Agent, or Firm*—Manfred Polk; Charles M. Caruso

[57] ABSTRACT

A process for preparing substantially pure enantiomers of formula (I)

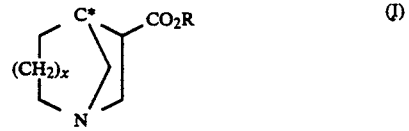

where the * represents a chiral center, x is 0 or 1, in exo-, endo- or a mixture of exo- and endo- forms; and R is hydrogen, alkyl or aralkyl, via diastereomers of formula (IIA) or (IIB);

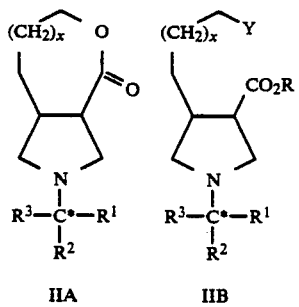

2 Claims, No Drawings

CHIRAL SYNTHESIS FOR PRODUCING 1-AZABICYCLO[2.2.1] HEPTANE-3-CARBOXYLATES

The present invention relates to a process for resolving enantiomers of compounds useful as intermediates in the synthesis of oxadiazoles having muscarinic agonist activity.

In European published patent specifications nos. 239309, 257741 and 261763 are disclosed certain azabicyclic compounds, including oxadiazole derivatives thereof, having for example, muscarinic agonist activity and processes for their preparation. The processes disclosed are multi-step and include those which proceed via intermediates of formula (A)

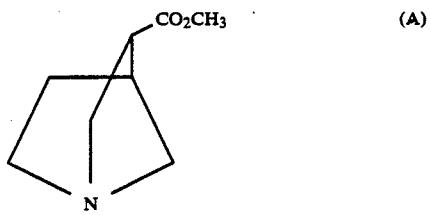

including analogues and derivatives thereof. Both the final azabicyclic compounds and the intermediates of formula (A) have at least one asymmetric centre and can therefore exist as both enantiomers and diastereomers. Some, such as the intermediate of formula (A), can exist as exo- and endo-isomers. However, no process is disclosed wherein the optical isomers of the final azabicyclic compounds (nor the intermediates of formula (A) nor its analogues and derivatives) can separately be prepared or the racemic mixture resolved.

Thus, in order to prepare individual enantiomers of the oxadiazoles mentioned above and other substituted azabicycles, attempts were made to resolve optically active intermediates used in their preparation. Various of the conventional methods were tried, but without complete success. For example, it was found that using chiral acids such as tartaric and camphor-10-sulphonic was unsuccessful. Likewise, the use of chiral esters such as derivatives of menthol, N-benzoyl-2-amino-1-butanol and N-benzoyl norephedrine did not work as either they could not be prepared or the chiral derivatives of the azabicycles would not separate. It was then surprising to find that a chiral amide of an intermediate could be prepared and could give rise to separation of the enantiomers, as desired.

The present invention is based on a novel intermediate of formula II having a removable N-substituent which possesses a chiral centre and provides a precursor for preparing a substantially pure enantiomer of a 1-azabicyclo[2.2.1]heptane or a 1-azabicyclo[3.2.1]octane substituted on the carbon atom β to the ring nitrogen by a carboxylic acid ester group. The diastereomers may be separated before continuing with the synthesis.

EP261763 describes a N-protected tetrahydropyrrole, which is cyclised to give a azabicyclo[2.2.1]heptane-3-carboxylic acid. However, the N-protecting group did not possess a chiral centre and there was no suggestion that the compound could be employed as a means of separating diastereomers at that stage.

The present process has the advantages of producing diastereomers of optically active intermediates which are capable of separation by standard means at more than one stage in their preparation and which, in several cases, are in crystalline form.

In particular, the present invention provides a process for preparing substantially pure enantiomers of formula (I)

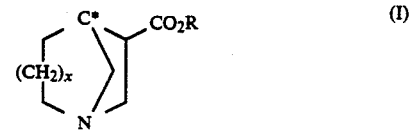

where the * represents a chiral centre, x is 0 or 1, in exo-, endo- or a mixture of exo- and endo- forms; and R is hydrogen, alkyl or aralkyl which process comprises:

(a) synthesising diastereomers of formula (IIA) or (IIB):

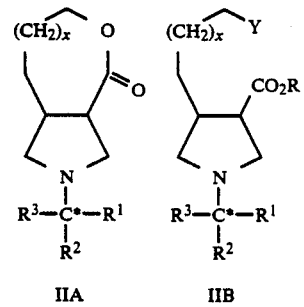

wherein $R^1$, $R^2$ and $R^3$ are each selected from H, alkyl, aryl and aralkyl, provided that $R^1$, $R^2$ and $R^3$ are each different from each other; R and x are as defined in formula (I); and Y is a leaving group;

(b) cyclising the diastereomer of formula IIA or IIB to the corresponding diastereomer of formula (III)

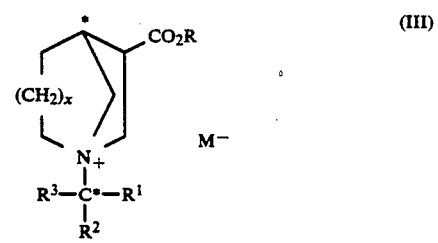

wherein R to $R^3$ are as in formula (I) and M is a counter ion;

(c) separating the diastereomers formed at step (a) or step (b);

(d) hydrogenation of the diastereomer of formula (III) to give the corresponding substantially pure enantiomer of formula (I); and optionally converting the enantiomer of formula (I) to a reactive derivative thereof.

$R^1$, $R^2$ and $R^3$ may be suitably selected from H, $C_{1-4}$ alkyl, phenyl, naphthyl and benzyl.

The preferred process is one wherein, in formula (II), $R^1$ is H, $R^2$ is methyl and $R^3$ is phenyl or naphthyl, preferably phenyl. Preferably R is $C_{1-4}$ alkyl or benzyl, in particular ethyl. Suitable leaving groups Y include bromo, and acetoxy.

The cyclisation step (b) (compound IIA or IIB to compound III) may be carried out using an alcohol, R—OH to produce compound III wherein R is alkyl or aralkyl; or using acetic acid to produce compound III where R is hydrogen. R—OH may be, for example, a lower alkanol having two or more carbon atoms optionally aryl substituted, such as ethanol, propanol or butanol. Preferably ROH is ethanol, propanol or butanol, especially ethanol.

The cyclisation is effected in the presence of an agent which will generate a cation at the carbon atom β to the ring carbonyl but which will not complex with the ring nitrogen, such as a hydrogen halide (e.g. HI, HBr). Preferably, HBr is used.

It is possible to separate the diastereomers of formula IIA/IIB or those of formula III. It is usually preferable to separate at the latter stage, as formula III is a quaternary salt, the diastereomers of which are more readily separable by means of fractional crystallisation. Any other separation technique may be used, for example chromatography.

The hydrogenation step (c) may be effected by hydrogen and a catalyst such as platinum or palladium or carbon, for example 5% or 10% palladium on carbon. Alternative methods such as transfer methods may also be employed such as using cyclohexene and an alcohol such as ethanol with a catalyst such as those mentioned above.

The final product enantiomers of formula (I) may be isolated in salt form such as the oxalate, maleate or hydrochloride salts. Once formed, the product enantiomers of formula (I) may, optionally be racemised to a mixture of the exo+endo isomers by, for example, base catalysed equilibration, or they may be used in the process described in our co-pending UK patent application no. 89110811.

Compounds of formula III and I, where R is alkyl or benzyl, may be hydrolysed to the corresponding compound where R is hydrogen. Compounds of formula I where R is hydrogen may be converted to any other reactive derivative thereof, such as the acid halide or anhydride, especially the acid chloride.

The process of this invention is therefore able to produce an enantiomer of formula I where $CO_2R$ represents a carboxylic acid group or a reactive derivative thereof.

Synthesis of the compound of formula (II) may be effected by reacting a pyranone of formula

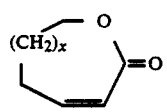

wherein x is as defined in formula (I) with an optically active aminoacetal of formula (IV):

wherein $R^1$ to $R^3$ are as defined in formula (II) and $R^4$ is $C_{1-6}$ alkyl or aryl (i.e. a substituent which cleaves on addition of the pyranone). Preferred substituents for $R^1$ to $R^3$ are as hereinbefore described for formula (III); $R^4$ is preferably methyl, propyl or butyl, more preferably methyl. The process is preferably carried out using the (+) optical isomer. Reaction of the pyranone with the optically active acetal of formula (IV) is effected optionally in the presence of an acid catalyst such as camphor sulphonic acid or preferably, trifluoroacetic acid.

Preparation of the optically active acetal (IV) is by methods analogous to those published in the art; for example, from an optically active silyl amine of formula (V):

wherein $R^1$ to $R^3$ are as defined in formula (II), by reaction with $R^4OH$ wherein $R^4$ is as defined in formula (IV) in the presence of an agent such as aqueous formaldehyde.

The optically active silyl amine (V) may itself be prepared by reacting an optically active amine of formula (VI)

wherein $R^1$ to $R^3$ are as defined in formula (II) with a silyl compound of formula $Me_3Si$—$CH_2$—X (wherein X is halo such as chloro) by methods analogous to those published in the art. The preferred optically active amine is R-(+)-α-methylbenzylamine.

The present invention further provides novel isomers of formulae (V), (IV), (II), (III) and (I) as hereinbefore defined. In addition, operating the process wherein, in formula (V), R is H provides a useful method of preparing non-chiral analogues of the compounds of formulae (II) and (IV).

The present invention will now be illustrated by the following examples, although other ways of putting it into effect will be clear from the foregoing description to the person skilled in the art.

EXAMPLE 1

(S)-(−)-N-1-(1-Naphthylethyl-N-trimethylsilylmethylamine, (V, $R^1$=H, $R^2$=Me, $R^3$=1-naphthyl)

(S)-(−)-1-(1-Naphthyl)ethylamine (12.5 g, 0.073 moles) and chloromethyltrimethylsilane (6.0 g, 0.049 moles) were gently heated together under reflux (ca. 105° C.) and under a nitrogen atmosphere. Heating was continued for 4 hours, the oil bath temperature reaching 185° C. The reaction mixture was cooled in a water bath, toluene (50 ml) added and the mixture made strongly basic by the addition of 15% potassium hydroxide solution (45 ml). The mixture was stirred vigorously, the layers separated and the aqueous layer extracted with toluene (2×50 ml). The organic phases were combined, dried ($K_2CO_3$) and evaporated under reduced pressure to an orange oil. Chromatography of the oil on silica gel with ethyl acetate followed by distillation (Kugelrohr) gave the amine as a colourless oil (8.4 g, 67%) b.p. 100° C./0.3 mbar (Found: C, 74.68; H, 9.05; N, 5.40. ($C_{16}H_{23}NSi$ requires C, 74.65; H, 9.00; N, 5.44%).

EXAMPLE 2

(R)-(+)-N-1-Phenylethyl-N-(methoxymethyl)trimethylsilylmethylamine (IV, $R^1$=H, $R^2$=$R^4$=Me, $R^3$=Ph)

(R)-(+)-N-1-Phenylethyl-N-trimethylsilylmethylamine (Padwa et al, Tetrahedron, 41,3529-3535 at p. 3532) (1.25 kg, 6.04 moles) was added to an ice-cooled mixture of methanol (232 g, 7.25 moles) and aqueous formaldehyde (37-40% w/w, 530 ml) over 30 minutes. The heterogeneous mixture was stirred at 0° C. for 2 hours then anhydrous potassium carbonate (240 g) was added and the mixture stirred for 30 minutes at 0° C. The layers were separated and the aqueous phase extracted with diethyl ether (2.5 l). The organic phases were dried ($Na_2SO_4$) and evaporated under reduced pressure at $\geq$30° C. to give the crude acetal (80% pure) as a colourless oil (1.46 kg, 96%) $\delta_C$ ($CD_2Cl_2$)-1.1 ($SiMe_3$), 19.61 (CMe), 40.38 ($NCH_2Si$), 54.91 (OMe), 62.51 (CH), 86.41 ($NCH_2O$), 127.13, 128.16, 128.61, 146.07 (Ph).

EXAMPLE 3

(S)-(−)-N-1-Phenylethyl-N-(butoxymethyl)trimethylsilylmethylamine (IV, $R^1$=H, $R^2$=Me, $R^3$=Ph, $R^4$=Bu)

The title compound was prepared from (S)-(−)-N-1-phenylethyl-N-trimethylsilylmethylamine by reaction with n-butanol and aqueous formaldehyde following the procedure of Example 2 to give the crude acetal (85% pure) as a colourless oil (7.1 g, 80%) $\delta_C$($CD_2Cl_2$)-1.09 ($SiMe_3$), 14.35, 20.16, 24.72, 67.38 (OBu), 19.57 (CMe), 40.30 ($NCH_2Si$), 62.30 (CH), 84.73 ($NCH_2O$), 127.01, 128.15, 128.51, 146.15 (Ph).

EXAMPLE 4

(R)-(+)-N-1-Phenylethyl-N-(butoxymethyl)trimethylsilylmethylamine (IV, $R^1$=H, $R^2$=Me, $R^3$=Ph, $R^4$=Bu)

The title compound was prepared from (R)-(+)-N-1-phenylethyl-N-trimethylsilylmethylamine by reaction with n-butanol and aqueous formaldehyde following the procedure of Example 2 to give the crude acetal (85% pure) as a colourless oil (34.2 g, 84%). The nmr spectrum was identical to the above (S)-isomer.

EXAMPLE 5

(S)-(−)-N-1-Phenylethyl-N-(octyloxymethyl)trimethylsilyl methylamine (IV, $R^1$=H, $R^2$=Me, $R^3$=Ph, $R^4$=Octyl)

The title compound was prepared from (S)-(−)-N-1-phenylethyl-N-trimethylsilylmethylamine by reaction with n-octanol and aqueous formaldehyde following the procedure of Example 2 to give the crude acetal (90% pure) as a colourless oil (9.1 g, 91%) $\delta_C$($CD_2Cl_2$)-1.28 ($SiMe_3$), 14.29, 23.08, 30.31, 29.74, 29.89, 26.82, 33.32, 63.13 (O Octyl), 19.37 (CMe), 40.11 ($NCH_2Si$), 62.10 (CH), 84.69 ($NCH_2O$), 126.82, 127.96, 128.31, 145.95 (Ph).

EXAMPLE 6

(S)-(−)-N-[1-(1-Naphthyl)ethyl]-N-methoxymethyltrimethylsilylmethylamine (IV, $R^1$=H, $R^2$=$R^4$=Me, $R^3$=1-naphthyl)

The title compound was prepared from (S)-(−)-N-1-(1-naphthyl)ethyl-N-trimethylsilylmethylamine by reaction with methanol and aqueous formaldehyde following the procedure of Example 2 to give the crude acetal (85% pure) as a colourless oil (3.6 g, 93%) $\delta_H$ [$(CD_3)_2CO$] 0.0 (s, $SiMe_3$), 1.57 (d, J 7 Hz, CMe), 2.18, 2.40 (AB quartet, J 15 Hz, $NCH_2Si$), 3.17 (s, OMe), 4.15, 4.30 (AB quartet, J 10 Hz, $NCH_2O$), 4.72 (q, J 7 Hz, CH), 7.4-8.5 (m, naphthyl).

EXAMPLE 7

(S)-(−)-N-[1-(1-Naphthyl)ethyl]-N-butoxymethyltrimethylsilylmethyl amine (IV, $R^1$=H, $R^2$=Me, $R^3$=1-naphthyl, $R^4$=Bu)

The title compound was prepared from (S)-(−)-N-1-(1-naphthyl)ethyl-N-trimethylsilylmethylamine by reaction with n-butanol and aqueous formaldehyde following the procedure of Example 2 to give the crude acetal (80% pure) as a pale yellow oil (5.5 g, 82%). $\delta_H$ [$(CD_3)_2CO$] 0.1 (s, $SiMe_3$), 0.93 (t, J 7 Hz, $CH_3CH_2$), 1.2-1.7 (m, $CH_3CH$ and $(CH_2)_2$), 2.22, 2.45 (AB quartet, J 15 Hz, $NCH_2Si$), 3.25 (t, J 7 Hz, $CH_2O$), 4.22, 4.35 (AB quartet, J 10 Hz, $NCH_2O$), 4.78 (q, J 7 Hz, CH), 7.3-8.5 (m, naphthyl).

EXAMPLE 8

2-[(R)-1-Phenylethyl]-4-oxo-1,2,3,6,7,7a-hexahydropyrano[3,4-c]pyrrole (IIA, $R^1$=H, $R^2$=Me, $R^3$=Ph, x=zero-two diasteromers)

(a) Crude (R)-(+)-N-1-phenylethyl-N-(methoxymethyl)trimethylsilylmethylamine (265 g, 0.84 moles) was added over 30 minutes to an ice-cooled, stirred solution of 5,6-dihydro-2H-pyran-2-one (100 g, 1.02 moles) and trifluoroacetic acid (0.5 ml) in ethyl acetate (1 l). The cooling bath was removed and an exotherm carried the reaction temperature to 60° C. The solution was stirred for 1 hour at 50°-60° C. then cooled to 20° C. Aqueous sodium bicarbonate (240 ml) was added and the layers separated. The aqueous phase was back extracted with ethyl acetate (2×250 ml) and the extracts combined, washed with water (100 ml), and dried ($Na_2SO_4$). The solvent was removed under reduced pressure and the residue dissolved in hot ethyl acetate (740 ml). A solution of maleic acid (118 g, 1.02 mole) in hot ethyl acetate (1.3 l) was added with stirring. Hexane (370 ml) was then added and the mixture seeded and allowed to cool. The slurry was aged at 5° C. for 1 hour then filtered and washed with ethyl acetate-hexane (5:1, 350 ml). The product was dried in vacuo to give the maleate salt as a colourless crystalline solid (288 g, 95%), m.p. 123°-125° C. The nmr spectrum showed the product to be a 1:1 mixture of cis diastereomers. The maleate salt (288 g) was added portionwise to a stirred mixture of ethyl acetate (1.25 l) and aqueous sodium bicarbonate (1.75 l). The mixture was stirred at 20° C. for a further 30 minutes then the layers were separated. The aqueous layer was extracted with ethyl acetate (1 l×2), the organic layers combined and dried ($Na_2SO_4$). The solution was evaporated under reduced pressure to afford the mixture of diastereomers as a yellow oil (195 g, 100% recovery). GC (12 m OV-1 column, 75° C. for 2 minutes then to 300° C. at 10° C./minute) Rt 16.1 minutes 99.4 area %.

(b) Similarly reaction of (R)-(+)-N-(1-phenylethyl-N-butoxymethyltrimethylsilylmethylamine with 5,6-dihydro-2H-pyran-2-one in the presence of trifluoroacetic acid gave the lactone (18.5 g, 72% yield) with a nmr spectrum identical to the above free base.

SEPARATION OF DIASTEREOMERIC LACTONES

A 1:1 mixture of the diastereomers (10.9 g) was crystallised from diethyl ether (30 ml). The product was dissolved in boiling diethyl ether (40 ml) and the hot solution concentrated to ~10 ml. The solution was allowed to cool and crystallise at 5° C. overnight. The product was collected by filtration, washed with cold diethyl ether (2×5 ml) and dried in vacuo to give the more polar diastereomer 2-[(S)-1-phenylethyl]-4-oxo-(3aR,7aS)-1,2,3,6,7,7a-hexahydropyrano[3,4-c]pyrrole as a colourless solid (2.2 g, 41%) m.p. 86°–87° C. (Found: C, 73.34; H, 7.80; N, 5.65. $C_{15}H_{19}NO_2$ requires C, 73.44; H, 7.81; N, 5.71%) $\delta^C$ [$(CD^3)_2CO$] 23.53 (7-$CH_2$), 27.53 (Me), 35.64 (7a-CH), 42.65 (3a-CH), 56.30 (1-$CH_2$), 59.82 (3-$CH_2$), 65.50 (CH), 67.61 (6-$CH_2$), 127.74, 129.17, 146.5 (Ph), 173.42 (CO).

The crystallisation liquors were evaporated to an oil and preparative HPLC (25 cm×21.2 mm Zorbax Sil column) with ethyl acetate gave the less polar diastereomer 2-[(S)-1-phenylethyl]-4-oxo-(3aS,7aR)-1,2,3,6,7,7a-hexahydropyrano[3,4-c]pyrrole as an oil (2.1 g, 40%). $\delta_C$ [$(CD_3)_2CO$] 23.70 (7-$CH_2$), 27.70 (Me), 35.76 (7a-CH), 42.67 (3a-CH), 58.86 (1-$CH_2$), 59.79 (3-$CH_2$), 65.59 (CH), 67.68 (6-$CH_2$), 127.83, 129.24, 146.5 (Ph), 173.40 (CO). A sample of the base was converted into the maleate salt m.p. 137°–139° C.

EXAMPLE 9

2-((S)-(−)-1-(1-Naphthyl)ethyl)-4-oxo-1,2,3,6,7,7a-hexahydropyrano[3,4-c]pyrrole (IIA, $R^1$=H, $R^2$=Me, $R^3$=1-naphthyl, x=zero)

(a) A 1M solution of trifluoroacetic acid in dichloromethane (1 ml) was added to a stirred solution of crude (S)-(−)-N-[1-(1-naphthyl)ethyl]-N-methoxymethyltrimethylsilylmethylamine (3.5 g, 9.9 mmol) and 5,6-dihydro-2H-pyran-2-one (1.3 g, 13.3 mmol) in dichloromethane (15 ml) at 0° C. The cooling bath was removed and a slight exotherm was noted. After 20 minutes no acetal remained. The reaction mixture was washed with saturated aqueous sodium bicarbonate (10 ml) and the aqueous solution back-extracted with dichloromethane (2×10 ml). The combined extracts were washed with saturated brine (10 ml), dried ($Na_2SO_4$) and evaporated under reduced pressure to give an orange oil. Chromatography on silica with ethyl acetate followed by Kugelrohr distillation gave the lactone as an oil (2.2 g, 76%) b.p. 70° C./0.2 mbar. $\delta_C$ [$(CD_3)_2CO$] 22.72 (7-$CH_2$), 27.70 (Me), 35.84, 36.93 (7a-CH), 42.74, 42.84 (3a-CH), 56.97, 57.08 (1-$CH_2$), 59.83, 60.06 (3-$CH_2$), 67.70 (6-$CH_2$), 124.90, 125.09, 125.37, 125.80, 126.22, 126.55, 128.19, 128.29, 129.22, 129.75, 147.80 (naphthyl).

The lactone (1.8 g, 6.1 mmol) was dissolved in t-butylmethylether (18 ml) and treated with maleic acid (0.7 g, 6.0 mmol) in ethyl acetate (7 ml). The crystalline product was filtered off, washed with t-butylmethylether (5 ml) and dried in vacuo to give the maleate salt (1.9 g, 76% recovery) m.p. 87°–98° C. (Found: C, 67.02; H, 6.16; N, 3.39. $C_{19}H_{21}NO_2.C_4H_4O_4$ requires C, 67.14; H, 6.12; N, 3.4%).

(b) Similarly reaction of (S)-(−)-N-[1-(1-naphthyl)ethyl]-N-butoxymethyltrimethylsilylmethylamine with 5,6-dihydro-2H-pyran-2-one in the presence of trifluoroacetic acid gave the lactone (2.2 g, 59%) with a nmr spectrum identical to the above product.

EXAMPLE 10

Cis-3-(2-Acetoxyethyl)-4-methoxycarbonyl-1-[(S)-1-phenylethyl]-pyrrolidine (IIB, R=Me, Y=MeCOO)

Potassium hydroxide (3.36 g, 60 mmoles) was added to a stirred solution of 5,6-dihydro-2H-pyran-2-one (4.9 g, 50 mmoles) in water (45 ml) at 5° C. The solution was allowed to warm to 20° C. and stirred for 2½ hours then evaporated to residue in a vacuum. The residue was flushed with isopropanol (2×50 ml) and dried in a vacuum at 50° C. over $P_2O_5$. This solid was slurried in dry dimethylformamide (30 ml) and methyl iodide (34.2 g, 240 mmol) added. The slurry was stirred for 18 hours at 20° C. then quenched by the addition of ice (20 g). The mixture was extracted with diethyl ether (4×50 ml) and the extracts washed with aqueous sodium chloride (50 ml) and dried ($Na_2SO_4$). Solvent removal in a vacuum afforded methyl (Z)-5-hydroxy-2-pentenoate as a colourless oil (4.1 g, 63% yield). The oil was dissolved in dichloromethane (40 ml) with N,N-dimethylaminopyridine (0.1 g) and treated with acetyl chloride (2.75 g, 35 mmoles) in dichloromethane (10 ml) added over 5 minutes at 5° C. The resulting slurry was allowed to warm to room temperature then quenched by the addition of water (40 ml) and the layers separated. The aqueous layer was extracted with dichloromethane (40 ml) and the organic extracts combined, washed with hydrochloric acid (0.5M, 2×50 ml) then water (2×50 ml), and dried ($Na_2SO_4$). Solvent removal in a vacuum followed by Kugelrohr distillation afforded methyl (Z)-5-acetoxy-2-pentenoate as a colourless oil (4.1 g, 76%) b.p. 75° C./0.1 mbar (Found: C, 55.60, H, 7.00 $C_8H_{12}O_4$ requires C, 55.80; H, 7.00%).

A solution of the crude (S)-(−)-N-1-phenylethyl-N-(butoxymethyl)trimethylsilylmethylamine (2.90 g) in dichloromethane (10 ml) was added to a solution of the acetoxy-ester (2.0 g, 11.6 mmoles) and trifluoroacetic acid (0.1 ml) in dichloromethane (20 ml). After 18 hours at room temperature aqueous sodium bicarbonate (25 ml) was added and the layers separated. The organic layer was dried ($Na_2SO_4$), evaporated to residue and the residue chromatographed on silica gel eluting with hexane-ethyl acetate (1:1). The early fractions gave the less polar isomer as an oil (0.75 g, 25% yield) $\delta_C$ [$(CD_3)_2CO$] 20.80 (MeCO), 23.83 (Me), 29.80 ($CH_2$), 38.72 (3-CH), 46.46 (4-CH), 51.54 (MeO), 55.83 (2-$CH_2$), 57.97 (5-$CH_2$), 63.57 ($CH_2O$), 65.92 (NCH), 127.64, 127.82, 129.32, 146.85 (Ph), 170.91 (CO), 174.47 (CO).

Later fractions gave the more polar isomer as an oil (0.63 g, 22% yield) $\delta_C$[$(CD_3)_2CO$] 20.58 (MeCO), 23.39 (Me), 29.37 ($CH_2$), 38.38 (3-$CH_2$), 46.36 (4-CH), 51.42 (MeO), 54.89 (2-$CH_2$), 58.59 (5-$CH_2$), 63.36 ($CH_2O$), 65.68 (NCH), 127.49, 127.65, 128.94, 146.0 (Ph), 171.0 (CO), 1740 (CO).

Other fractions gave a mixture of isomers as an oil (0.57 g, 20% yield).

EXAMPLE 11

Ethyl 1-azoniabicyclo[2.2.1]heptane-3-carboxylate esters (III, R=Et, R$^1$=H, R$^2$=Me, R$^3$=Ph, x=zero, M$^-$=Br$^-$)

(a) Ethyl 1-[(S)-1-phenylethyl]-(3R,4S)-1-azoniabicyclo[2.2.1-]heptane-3-carboxylate bromide The "more polar" 2-[(S)-1-phenylethyl]-4-oxo-(3aR,-7aS)-1,2,3,6,7,7a-hexahydropyrano[3,4-c]pyrrole (3.30 g, 13.5 mmoles) was dissolved in absolute ethanol (180 ml) and the clear solution saturated with anhydrous hydrogen bromide gas. The solution was heated at reflux temperature for 4 hours, then cooled and evaporated to residue under reduced pressure to give the bromoethyl pyrrolidine (VII, R=Et, X=Br) as the hydrobromide salt. The residue was cooled in an ice-bath and basified by cautious addition of saturated aqueous sodium bicarbonate. The product was extracted into chloroform (3×100 ml), dried (Na$_2$SO$_4$), and the solvent removed under reduced pressure. The gummy residue was flushed with ethanol (3×100 ml) to give the quaternary salt as a colourless crystalline solid (4.8 g, 100%) δ$_C$ [(CD$_3$)$_2$CO] 16.15, 62.09 (CH$_3$CH$_2$O), 14.41 (Me), 24.80 (5-CH$_2$), 38.87 (4-CH), 43.19 (3-CH), 57.89 (2-CH$_2$), 59.94 (6-CH$_2$), 66.29 (CHN$^+$), 66.61 (7-CH$_2$), 129.27, 130.75, 130.84 (Ph).

(b) Ethyl 1-[(S)-1-phenylethyl]-(3S,4R)-1-azoniabicyclo[2.2.1-]heptane-3-carboxylate bromide Similarly, the less polar (3aS,7aR) lactone (1.8 g, 7 mmoles) in ethanol saturated with hydrogen bromide gave the quaternary salt (2.5 g, 96%) δ$_C$(CD$_2$Cl$_2$) 12.62, 60.39 (CH$_3$CH$_2$O), 14.78 (Me), 23.39 (5-CH$_2$), 37.06 (4-CH), 42.94 (3-CH), 55.39 (2-CH$_2$), 58.85 (6-CH$_2$), 64.29 (CHN$^+$), 64.48 (7-CH$_2$), 127.85, 128.45, 128.88, 132.63 (Ph), 166.78 (CO).

(c) Ethyl 1-[(R)-1-phenylethyl]-(3S,4R)-1-azoniabicyclo[2.2.1-]heptane-3-carboxylate bromide Similarly a 1:1 mixture of 2-[(R)-1-phenylethyl]-4-oxo-(3aR,7aS)-1,2,3,6,7,7a-hexahydropyrano[3,4-c]pyrrole and the (3aS,7aR)-isomer (139 g, 0.57 moles) in ethanol (1.39 l) saturated with hydrogen bromide gave a mixture of the (3S,4R) and (3R,4S) quaternary salts (189 g) in 94% yield. The crude mixture was dissolved in boiling ethanol (90 ml), and ethyl acetate (810 ml) added to the hot solution. Cooling gave a crystalline solid (69.0 g) which was suspended in boiling acetone (640 ml) for 1 hr. The suspension was cooled to 5° C. for 2 hrs, then filtered to give the (3S,4R) quaternary salt as a colourless solid (64.0 g, 32%) m.p. 160°-161° C., [α]$_D$ +21° (c 0.5 in EtOH).

(d) Ethyl 1-[(S)-1-phenylethyl]-1-azoniabicyclo[2.2.1]heptane-3-carboxylate bromide, as a mixture of (3R,4S) and (3S,4R) isomers, from acetoxyethyl pyrrolidine (VII)

Cis-3-(2-Acetoxyethyl)-4-methoxycarbonyl-1-[(S)-1-phenylethyl]-pyrrolidine (0.5 g) in ethanol (25 ml) saturated with hydrogen bromide gave the mixture of quaternary salts (0.55 g) in quantitative yield.

EXAMPLE 12

Propyl 1-[(R)-1-phenylethyl]-(3S,4R)-1-azoniabicyclo[2.2.1-]heptane-3-carboxylate bromide (III, R=Pr, R$^1$=H, R$^2$=Me, R$^3$=Ph, x=zero, M$^-$=Br$^-$)

A solution of 2-[(R)-1-phenylethyl]-4-oxo-1,2,3,6,7,7a-hexahydropyrano[3,4-c]pyrrole isomers (5.8 g) in n-propanol (116 ml) was saturated with hydrogen bromide gas and heated under reflux overnight. The solvent was removed in vacuo and the residue treated with saturated aqueous sodium bicarbonate (150 ml). The mixture was extracted with chloroform (3×100 ml), dried (Na$_2$SO$_4$), and evaporated to residue in vacuo. Crystallisation from acetone-ethyl acetate (1:1) afforded a 4:1 diastereomeric mixture (3S,4R:3R,4S) of the quaternary salts. Recrystallisation from acetone (9 mlg$^{-1}$) afforded the pure (3S,4R) isomer as a colourless crystalline solid (1.3 g, 30%) m.p. 144°-146° C. δ$_C$ (CD$_2$Cl$_2$) 10.48, 22.25, 66.56 (CH$_3$CH$_2$CH$_2$O), 16.45 (Me), 24.83 (5-CH$_2$), 38.66 (4-CH), 45.12 (3-CH), 57.91 (2-CH$_2$), 59.70 (6-CH$_2$), 66.36 (CHN$^+$), 67.75 (7-CH$_2$), 129.70, 130.41, 130.78, 132.21 (Ph), 170.90 (CO), [α]$_D$ +22.6° (c 0.5 in EtOH).

EXAMPLE 13

Butyl 1-[(R)-1-phenylethyl]-(3S,4R)-1-azoniabicyclo[2.2.1-]heptane-3-carboxylate bromide (III, R=Bu, R$^1$=H, R$^2$=Me, R$^3$=Ph, x=zero, M$^-$=Br$^-$)

A solution of 2-[(R)-1-phenylethyl]-4-oxo-1,2,3,6,7,7a-hexahydropyrano[3,4-c]pyrrole isomers (5.0 g) in n-butanol (100 ml) was saturated with hydrogen bromide gas and heated under reflux overnight. The solvent was removed in vacuo and the residue treated with aqueous sodium bicarbonate (150 ml) and extracted with chloroform (3×100 ml). The extract was dried (Na$_2$SO$_4$) and evaporated to residue in vacuo. The crude product was chromatographed on silica gel eluting with ethyl acetate-methanol (3:1) then crystallised from ethyl acetate-acetone (4:1) to give the (3S,4R) salt as a colourless solid (1.06 g, 27%). m.p. 92°-94° C. δ$_C$ (CD$_2$Cl$_2$) 13.81, 19.45, 30.69, 66.08 (CH$_3$CH$_2$CH$_2$CH$_2$O), 16.42 (Me), 24.83 (5-CH$_2$), 38.62 (4-CH), 45.17 (3-CH), 57.86 (2-CH$_2$), 59.75 (6-CH$_2$), 66.22 (CHN$^+$), 66.52 (7-CH$_2$), 129.67, 130.36, 130.76, 134.15 (Ph), 170.81 (CO), [α]$_D$ +22.9° (c 0.5 in EtOH).

EXAMPLE 14

Ethyl 1-[(S)-1-Naphthylethyl]-1-azoniabicyclo[2.2.1]heptane-3-carboxylate bromide (III, R=Et, R$^1$=H, R$^2$=Me, R$^3$=1-naphthyl, x=zero, M$^-$=Br$^-$)

2-[(S)-1-(1-Naphthyl)ethyl]-4-oxo-1,2,3,6,7,7a-hexahydropyrano[3,4-c]pyrrole (3.8 g, 12.9 mmol) was dissolved in absolute ethanol (114 ml) and the solution saturated with anhydrous hydrogen bromide (60 g). An exotherm carried the temperature to reflux. The mixture was heated under reflux for 15 hours after which time tlc (alumina, MeOH-EtOAc, (1:1), I$_2$) indicated no starting material remained. The mixture was cooled and evaporated to residue under reduced pressure (temp. <40° C.). The residue was cooled in an ice bath and basified by the careful addition of saturated, aqueous sodium bicarbonate (100 ml). The product was extracted into chloroform (2×100 ml), the organic phases combined, dried (Na$_2$SO$_4$) and evaporated to residue under reduced pressure. Chromatography on alumina with ethyl acetate then ethyl acetate:methanol (9:1) gave a 1:1 mixture of diastereomers (2.1 g, 40%). $\delta_H$ [(CD$_3$)$_2$CO] 1.0–1.3 (m, CH$_3$CH and CH$_3$CH$_2$), 1.65 (m, 5-CH$_2$), 2.0 (m, 4-CH), 3.0–4.5 (m, 2-, 6-, 7-CH$_2$ and 3-CH), 4.1 (2 x q, CH$_2$O), 6.69 (2 x q, CH), 7.4–9.5 (m, naphthyl).

EXAMPLE 15

Ethyl (3R,4S)-1-azabicyclo[2.2.1]heptane-3-carboxylate oxalate (I, R=Et, x=zero)

Ethyl 1-[(S)-1-phenylethyl]-(3R,4S)-1-azoniabicyclo[2.2.1]heptane-3-carboxylate bromide (4.8 g, 13.5 mmoles) in ethanol (200 ml) containing acetic acid (3 ml) was shaken with 10% palladium on carbon (0.6 g) under a hydrogen atmosphere (150 psi) for 48 hours at 20° C. The catalyst was removed by filtration and washed with ethanol (3×50 ml). The combined filtrates were evaporated to residue under reduced pressure at ≦40° C. The solid residue was cooled in an ice-bath and basified by addition of saturated aqueous sodium bicarbonate (20 ml). Chloroform (100 ml) was added, followed by sufficient water (10 ml) to give two clear layers. The layers were separated and the aqueous phase extracted with chloroform (2×100 ml). The combined extracts were dried (Na$_2$SO$_4$), evaporated to residue under reduced pressure, and flushed with isopropanol (20 ml). A solution of anhydrous oxalic acid (1.22 g, 13.5 mmoles) in isopropanol (20 ml) was added and the mixture heated to give a clear solution. The solution was allowed to cool and crystallise at room temperature, then aged at 5° C. for 1 hour. The solid was filtered, washed with cold isopropanol (2×10 ml), and dried in a vacuum at 40° C. to give the oxalate salt as a colourless crystalline solid (2.9 g, 84%), m.p. 130°–132° C. (Found: C, 50.81; H, 6.59; N, 5.42. C$_9$H$_{15}$NO$_2$.C$_2$H$_2$O$_4$ requires C, 50.96; H, 6.61; N, 5.40%); $[\alpha]_D$ −32° (c 0.5 in EtOH); $\delta_C$(free base in (CD$_3$)$_2$CO) 13.52, 59.67 (CH$_3$CH$_2$O), 24.88 (5-CH$_2$), 40.72 (4-CH), 46.12 (3-CH), 53.25 (6-CH$_2$), 55.86 (7-CH$_2$), 59.67 (2-CH$_2$), 173.64 (CO).

EXAMPLE 16

Ethyl (3S,4R)-1-azabicyclo[2.2.1]heptane-3-carboxylate hydrobromide (I, R=Et, x=zero)

Ethyl 1-[(R)-1-phenylethyl]-(3S,4R)-1-azoniabicyclo[2.2.1]heptane-3-carboxylate bromide (600 g, 1.69 moles) and cyclohexene (2.4 l) in ethanol (15 l) were heated with 10% palladium on charcoal (60 g) at reflux temperature for 18 hours. The slurry was cooled to 20° C. and filtered. The apparatus was rinsed with ethanol (2×1 l) and the filtrates combined and evaporated to residue in vacuo to give the hydrobromide salt as a colourless crystalline solid (400 g, 94%), m.p. 168°–170° C. (Found: C, 43.35, H, 6.40; N, 5.55. C$_9$H$_{15}$NO$_2$.HBr requires C, 43.21; H, 6.45; N, 5.60%); $[\alpha]_D$ +30.1° (c 0.5 in EtOH); $\delta_C$ (CD$_3$OD) 12.54 (CH$_3$), 22.55 (5-CH$_2$), 38.50 (4-CH), 43.09 (3-CH), 51.70 (6-CH$_2$), 53.58 (7-CH$_2$), 60.77 (CH$_2$O), 169.94 (CO).

EXAMPLE 17 endo (3S,4R)-1-Azabicyclo[2.2.1]heptane-3-carboxylic acid, hydrobromide (1, R=H, x=zero)

endo Ethyl (3S,4R)-1-azabicyclo[2.2.1]heptane-3-carboxylate hydrobromide (840 g, 3.36 moles) in concentrated hydrochloric acid (5.3 l) was heated under reflux for 5 hours and allowed to cool to room temperature overnight. The solution was evaporated and the residue dried in vacuo over phosphorus pentoxide to give the acid hydrobromide salt as a solid (688 g, 92%), m.p. 230°–233° C. $[\alpha]_D$ +28.8° (c I in MeOH); $\delta_C$(CD$_3$OD) 22.54 (5-CH$_2$), 38.36 (4-CH), 42.97 (3-CH), 51.63 (6-CH$_2$), 53.63 (7-CH$_2$), 59.67 (2-CH$_2$), 171.14 (CO).

We claim:

1. A process for preparing substantially pure enantiomers of formula (I)

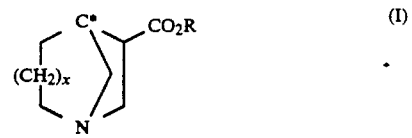

where the * represents a chiral centre, x is o or 1, in exo-, endo- or a mixture of exo- and endo- forms; and R is hydrogen, alkyl or aralkyl, said process comprises:
  (a) synthesising diastereomers of formula (IIA) or (IIB):

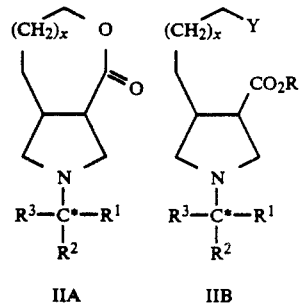

wherein R$^1$, R$^2$ and R$^3$ are each selected from H, alkyl, aryl and aralkyl, provided that R$^1$, R$^2$ and R$^3$ are each different from each other; R and x are as defined in formula (I) above; and Y is a leaving group;
  (b) cyclising in the presence of an agent which will generate a cation at the carbon atom β to the ring carbonyl which will not complex with the ring nitrogen the diastereomer of formula IIA or IIB to the corresponding diastereomer of formula (III)

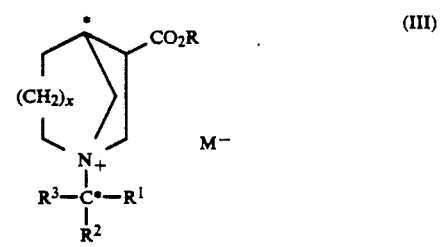

wherein R to R$^3$ are as in formula (I) and M is a counter ion;
  (c) separating the diastereomers formed at step (a) or step (b);
  (d) hydrogenation of the diastereomer of formula (III) to give the corresponding substantially pure enantiomer of formula (I); and
  optionally converting the enantiomer of formula (I) to a reactive derivative thereof.

2. A process as claimed in claim 1 wherein R$^1$ is hydrogen, R$^2$ is methyl and R$^3$ is phenyl or naphthyl.